(12) United States Patent
Wang (10) Patent No.: US 8,131,045 B2
(45) Date of Patent: Mar. 6, 2012

(54) IMAGE PROCESSING APPARATUS, IMAGE PROCESSING METHOD AND RECORDING MEDIUM

(75) Inventor: Caihua Wang, Minato-ku (JP)

(73) Assignee: Fujifilm Corporation, Tokyo (JP)

( * ) Notice: Subject to any disclaimer, the term of this patent is extended or adjusted under 35 U.S.C. 154(b) by 897 days.

(21) Appl. No.: 12/146,789

(22) Filed: Jun. 26, 2008

(65) Prior Publication Data

US 2009/0003677 A1    Jan. 1, 2009

(30) Foreign Application Priority Data

Jun. 27, 2007  (JP) ................. 2007-169340

(51) Int. Cl.
*G06K 9/00* (2006.01)
(52) U.S. Cl. .......................... 382/131; 378/4
(58) Field of Classification Search .................. 382/131, 382/128; 378/4–20, 901
See application file for complete search history.

(56) References Cited

U.S. PATENT DOCUMENTS

2006/0062425 A1* 3/2006 Shen et al. ................. 382/100

FOREIGN PATENT DOCUMENTS

| JP | 2000-287964 A | 10/2000 |
|---|---|---|
| JP | 2001-022921 A | 1/2001 |
| JP | 2001-137228 A | 5/2001 |
| JP | 2004-173748 A | 6/2004 |
| JP | 2005-332397 A | 12/2005 |
| JP | 2007-111533 A | 5/2007 |
| JP | 2007-111534 A | 5/2007 |

OTHER PUBLICATIONS

Foreign Office Action dated Mar. 17, 2010, corresponding to Application No. JP 2007-169340.
Notice of Reasons for Rejection, dated Jun. 2, 2010, issued in corresponding JP Application No. 2007-169340, 6 pages in English and Japanese.
Notice of Reasons for Rejection, dated Aug. 19, 2010, issued in corresponding JP Application No. 2007-169340, 8 pages in English and Japanese.

* cited by examiner

*Primary Examiner* — Hoon Song
(74) *Attorney, Agent, or Firm* — Sughrue Mion, PLLC (57) ABSTRACT

An image processing apparatus includes: a recognizing device which recognizes a bone area extracted from a tomogram, the bone area including a bone site composed of several bone pieces, in units of bone pieces; a display site selecting device which selects a bone site to be displayed; a display/non-display determining device which determines a bone piece to be displayed with respect to the selected bone site; and a display controlling device which controls to display a bone piece corresponding to the selected bone site based on the determination by the display/non-display determining device.

Thus, only a selection of a bone site to be displayed allows a display of the selected bone site in units of bone pieces.

5 Claims, 7 Drawing Sheets

☐ RIGHT FIRST RIB       ☐ STERNUM
☐ RIGHT SECOND RIB      ☐ FIRST LUMBAR VERTEBRA
☐ . . .                 ☐ SECOND LUMBAR VERTEBRA
☐ FIRST CERVICAL VERTEBRA  ☐ SACRUM
☐ SECOND CERVICAL VERTEBRA ☐ . . .

[ ADD MENU ]            [ DELETE MENU ]

NAME: [                        ]

FIG.9

|  | PIECE 1 | PIECE 2 | . . . | PIECE n |
|---|---|---|---|---|
| SITE 1 | 1 | 0 |  | 1 |
| SITE 2 | 0 | 1 |  | 1 |
| . . . | 1 | 0 |  | 0 | ured images
IMAGE PROCESSING APPARATUS, IMAGE PROCESSING METHOD AND RECORDING MEDIUM

BACKGROUND OF THE INVENTION

1. Field of the Invention

The present invention relates to an image processing apparatus, an image processing method, and recording medium on which a program causing a computer to perform the steps of the method is recorded. More specifically, the present invention relates to an image processing apparatus, an image processing method and a recording medium for displaying a bone site specified from a bone area extracted from a tomogram image, in units of bone pieces.

2. Description of the Related Art

Conventionally, tomograms of human body such as CT (Computer Tomography), MRI (Magnetic Resonance Imaging), and PET (Positron Emission Tomography) have been widely used for medical diagnosis, and Computer Aided Diagnosis of Medical Images is known.

In the diagnosis, a bone area is automatically extracted from an X-ray CT image as a preprocessing for displaying a MIP (Maximum Intensity Projection) image, recognizing a bone number, or displaying a bone.

In order to confirm of the result of the automatic extraction of a bone, the generally known volume rendering approach is often used. However, when the object is a skeleton composed of complicated structures, depending on a view position for displaying the image, a plurality of structures are overlapped to each other, and sometimes partly hidden away from the image. In such a case, only a part of the skeleton can be desirably displayed to prevent any hide away.

To address the above problem, conventionally, an approach has been known that divides a plurality of sites or one site into a plurality of objects to selectively display the site.

For example, Japanese Patent Application Laid-Open No. 2001-22921 describes a three dimensional image displaying apparatus in which a group of object parameters including object parameters for specifying a space area, an opacity, a color of an object and projection processing parameters is switched, so that an image of a new group of objects can be updated and displayed in a plurality of image display regions at one time or in an extremely short period of time.

Also, for example, Japanese Patent Application Laid-Open No. 2000-287964 describes a three dimensional image displaying apparatus in which not only the sites having different physical characteristics from each other but also the sites having identical physical characteristics to each other can be separately displayed as a plurality of objects, and also an object to be displayed is selectable for display from a plurality of objects.

SUMMARY OF THE INVENTION

However, the approaches described in the above two Japanese patents had a problem that a manual setting of a plurality of objects was required and the operation took time and effort.

The present invention was made in view of the above situation, and one object of the present invention is to provide an image processing apparatus, an image processing method and a recording medium on which a program causing a computer to perform the steps of the method is recorded which enable to set an area of an object without any complicated operation, and to readily display only a part of skeleton of the object a user wants to display.

In order to achieve the purpose, according to a first aspect of the present invention, an image processing apparatus comprises: a recognizing device which recognizes a bone area extracted from a tomogram, the bone area including a bone site composed of several bone pieces, in units of bone pieces; a display site selecting device which selects a bone site to be displayed; a display/non-display determining device which determines a bone piece to be displayed with respect to the selected bone site; and a display controlling device which controls to display a bone piece corresponding to the selected bone site based on the determination by the display/non-display determining device.

This enables an easy display of a bone site a user wants to display in units of bone pieces when the user only selects a bone site to be displayed. The term "tomogram" as used herein includes X-ray CT images, and synthesized images from CT images and other tomograms which are taken by modality, such as a synthesized image from an X-ray CT image and a PET image (for example, a PET/CT fusion image).

Furthermore, according to a second aspect of the present invention, the image processing apparatus according to the first aspect, further comprises a correspondence relationship table predefining a correspondence relationship between bone site and bone piece to indicate if respective bone piece is to be displayed or not with respect to a bone site, and the display/non-display determining device determines the bone piece to be displayed with reference to the correspondence relationship table.

This enables an easy display of a bone site a user wants to display in units of bone pieces when the user only selects a predefined bone site.

In addition, according to a third aspect of the present invention, the image processing apparatus according to the second aspect of the present invention further comprises a changing device which changes the correspondence relationship table.

This allows a user to freely define a bone site the user wants to display so that the bone site can be displayed in units of bone pieces.

Similarly, in order to achieve the above purpose, according to a fourth aspect of the present invention, an image processing method comprises steps of: recognizing a bone area extracted from a tomogram, the bone area including a bone site composed of several bone pieces, in units of bone pieces; selecting a bone site to be displayed; determining a bone piece to be displayed with respect to the selected bone site; and controlling to display a bone piece corresponding to the selected bone site based on the determination result.

This enables an easy display of a bone site a user wants to display in units of bone pieces when the user only selects a bone site the user wants to display.

Further, according to a fifth aspect of the invention, a recording medium on which a program causing a computer to perform the steps of the method according to the fourth aspect is recorded, is provided. This can also achieve the above purpose by causing the computer on which the program is installed to execute the program.

As described above, according to the aspects of the present invention, when a user only selects a bone site he/she wants to display, a part of the bone can be readily displayed in units of bone pieces.

DETAILED DESCRIPTION OF THE PREFERRED EMBODIMENTS

Now, an image processing apparatus and an image processing method according to the present invention will be explained in detail below with reference to the drawings. In the following embodiments, an X-ray CT image is used for explanation, but the present invention may be also applied to an image such as a synthesized image from an X-ray CT image and a PET image.

Figure 1:
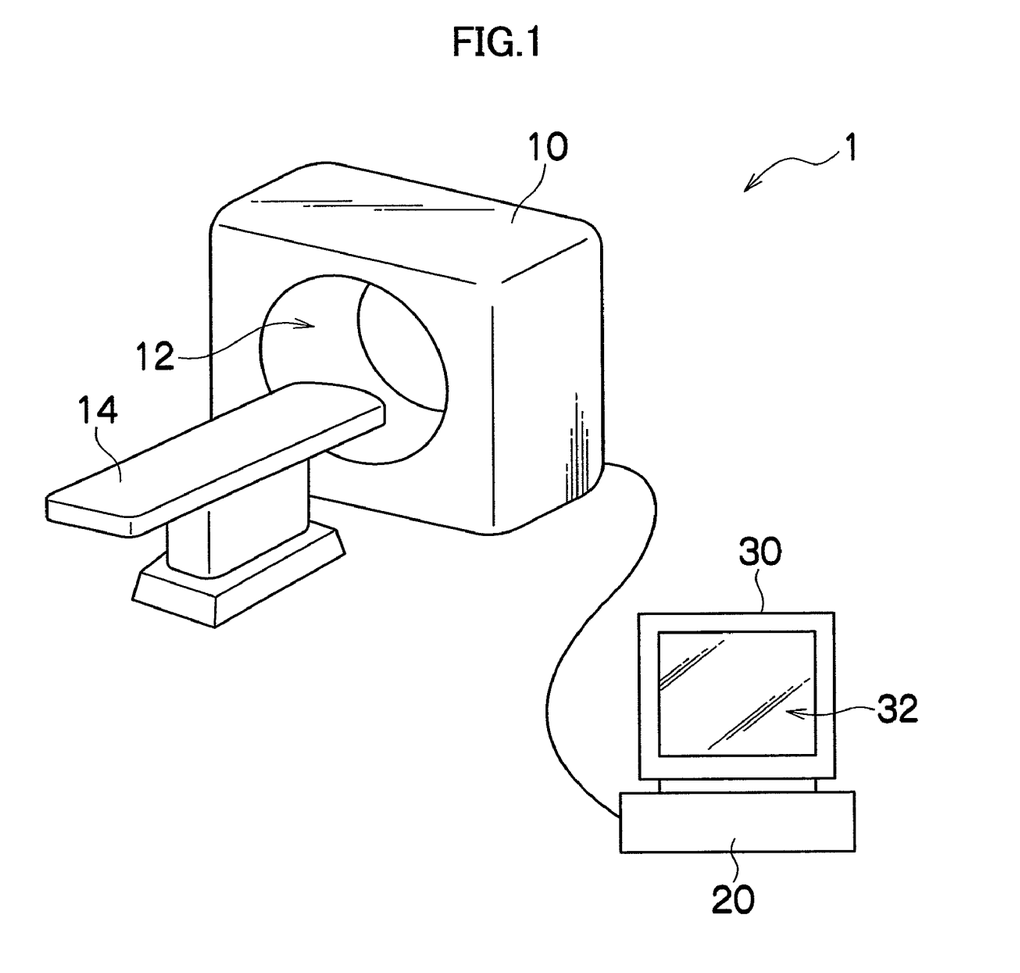
FIG. 1 is a structural diagram showing an outline of an X-ray CT apparatus according to the present invention which performs image processings for extracting a bone area from a CT image and displaying a bone in units of pieces.

FIG. 1 is a structural diagram showing an outline of an X-ray CT apparatus according to the present invention which performs image processings for extracting a bone area from a CT image and displaying a bone in units of pieces.

As shown in FIG. 1, an X-ray CT apparatus 1 generally includes: a scanner gantry section 10 which takes a CT slice image; an image processing section 20 which performs various image processings to the obtained CT slice image; and an image displaying section 30 which displays the processed CT image.

The scanner gantry section 10 has an opening 12 formed therein, so that a subject (not shown) lying on a bed 14 which is provided to the opening 12 is subjected to X-ray radiation and detection to take a CT slice image of the subject.

In addition, not shown in detail, but around the opening 12 of the scanner gantry section 10, rotatable circular plates are provided which has an X-ray tube for radiating X-ray, and an X-ray detector opposing to the X-ray tube so that an X-ray is radiated to a cross section of a subject to take a CT image thereof while the rotatable circular plates are rotated around the subject who is lying on the bed 14. The relative position of the rotatable circular plate to the subject is often changed and a taking of CT images (slice images) is repeated for each cross section of the subject, so as to obtain a plurality of image data.

The image processing section 20 receives CT slice images taken by the scanner gantry section 10, and performs image processings to the images according to the present invention.

The image displaying section 30 has a display screen 32 such as an LCD (liquid crystal display) and a CRT (Cathode Ray Tube) for displaying an image, and displays a CT slice image or a reference screen by which a user inputs an indication, or displays a bone selected by a user in units of pieces, which will be explained later in detail.

Figure 2:
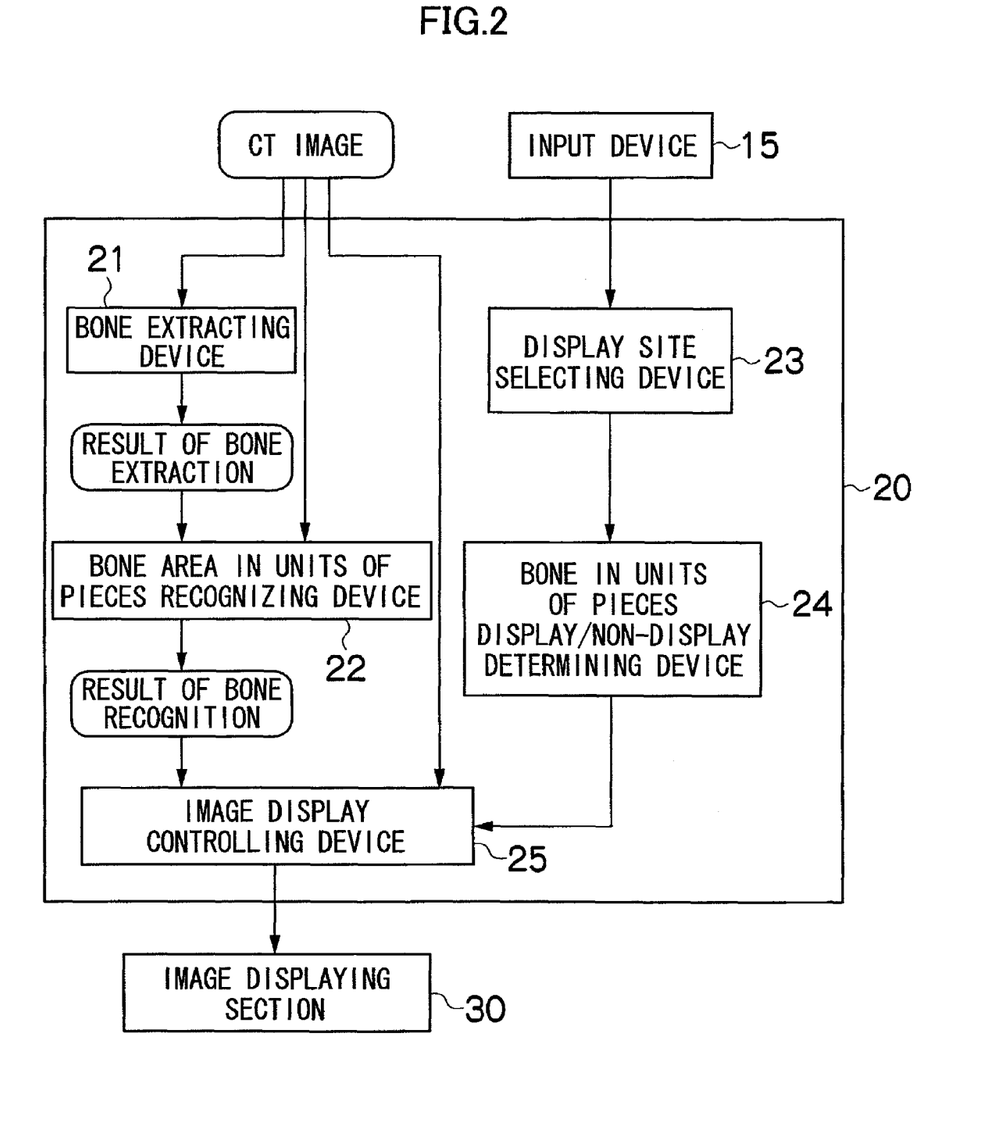
FIG. 2 is a structural diagram showing the detail of image processing sections.

FIG. 2 shows the detail structure of the image processing sections 20.

As shown in FIG. 2, the image processing section 20 of the present embodiment generally includes a bone extracting device 21, a bone area in units of pieces recognizing device 22, a display site selecting device 23, a bone in units of pieces display/non-display determining device 24, and an image display controlling device 25.

The bone extracting device 21 extracts a bone area from a CT slice image taken by the scanner gantry section 10. The approach for the extraction is not limited to any particular one, and any generally known method for extracting a bone may be used.

The bone area in units of pieces recognizing device 22 recognizes a bone in units of pieces from an extracted bone area, such as vertebra, rib, and pelvis. The display site selecting device 23 selects a bone site a user wants to display, via an input device 15 such as keyboard and mouse, with reference to the display screen 32.

The term "site" as used herein is comprised of several pieces, and is a broader term to a piece. That is, when a user selects a bone site he/she wants to display, the pieces of the bone which comprise the site are displayed. For example, when the site is rib, the pieces of the site include a first rib to a twelfth rib, and when the site is vertebra, the pieces of the site correspond to twenty-four bone pieces, including: a first to a seventh cervical vertebra; a first to a twelfth thoracic vertebra; and a first to a fifth lumbar vertebra. The detail will be described later, but in addition to the correspondence relationship between site and pieces which are anatomically determined as described above, a user may define a correspondence relationship between site and pieces by specifying pieces and putting a name on the site of the pieces. Furthermore, a user may gather several sites into a group, and define the group as a new site.

The bone in units of pieces display/non-display determining device 24 determines whether to display or non-display a piece which corresponds to a site a user selects. The detail will be described later, but for example, a table defining a correspondence relationship which indicates a display/non-display of a respective piece with respect to a respective site is set in a system in advance, so that the bone in units of pieces display/non-display determining device 24 refers to the table to determine the display/non-display of a respective piece of a selected site.

The image display controlling device 25 controls the image displaying section 30 to display a bone site selected from CT image data by a user, in units of bone pieces, based on a result of bone recognition by the bone area in units of pieces recognizing device 22 and data by bone in units of pieces display/non-display determining device 24. As a result of the control, the image displaying section 30 displays only the area corresponding to the piece which was determined to display by the bone in units of pieces display/non-display determining device 24.

Now, operations of the present embodiment will be explained below.

First, the bone extracting device 21 extracts a bone area from an input CT image. As described above, the method for extracting a bone in the bone extracting device 21 is not limited to any particular one, and any known method may be used.

For example, a method in which a bone area is extracted by comparing a profile of pixel values of a bone in a CT image with a predetermined threshold is known. Alternatively, when a rib is extracted, a method in which an edge image is generated from a chest image of a subject using an edge extracting filter, and a parabola that seems to indicate a rib is found from the edge image using Hough transform for parabola detection for example so as to detect a rib shape is known.

The result of a bone extraction by the bone extracting device 21 is sent to the bone area in units of pieces recognizing device 22

Then the bone area in units of pieces recognizing device 22 first recognizes individual sites for each CT slice image. That is, for each CT slice image data, the bone areas included therein are individually categorized into cervical part, shoulder, chest and abdominal part, pelvis, foot, and the like.

Next, the bone areas are recognized in units of pieces. A unique label which is determined in advance is given to each bone piece.

For example, a method for recognizing vertebra will be explained below with reference to figures.

Figure 3:
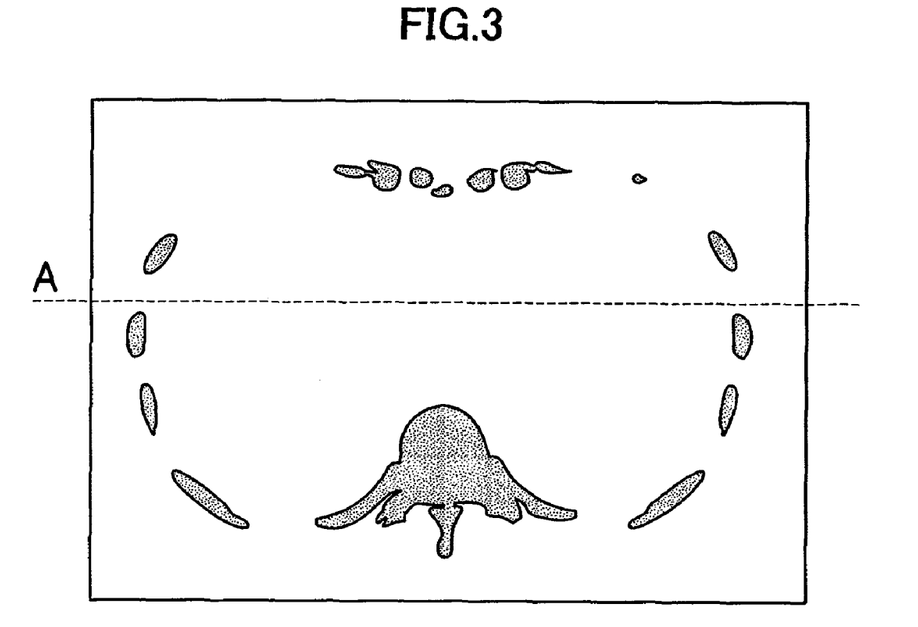
FIG. 3 is an explanatory diagram showing a CT slice image of a vertebra part.

FIG. 3 shows a CT slice image of vertebra part. First, a center line of the vertebra and a lateral width of the vertebra are obtained. In order to obtain these parameters, among the bone areas in FIG. 3, a region under a center line A in the longitudinal direction of the body surface (the line in the lateral direction of a body perpendicular to a front-back direction of the body located at the center of the front-back direction in a cross section which is perpendicular to the direction of body axis between a head and a foot) is projected onto the horizontal axis to generate a density histogram.

Figure 4:
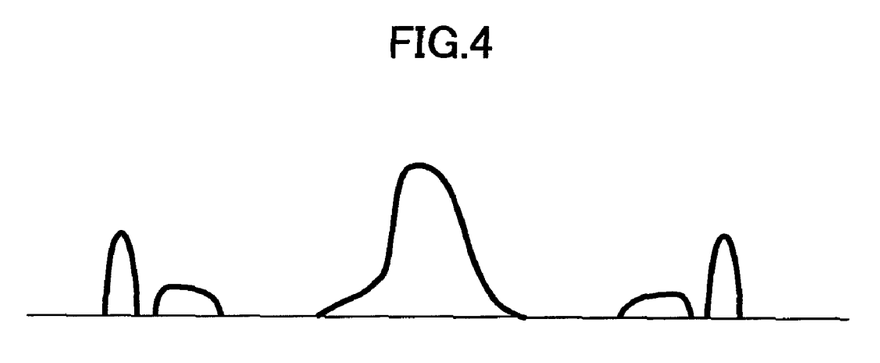
FIG. 4 is a diagram showing a density histogram of a bone area which is lower than the center line A of the slice image of FIG. 3.

FIG. 4 shows a density histogram of bone areas generated as described above. In the histogram shown in FIG. 4, a large peak appears at the center, and smaller peaks are formed on both sides of the large peak. In the case of the bone area shown in FIG. 3, it is presumed that the rib part forms the smaller peaks, and that the vertebra having bone components most therein forms the largest peak. Therefore, the largest peak at the center of the histogram of FIG. 4 is detected, and a vertebral area corresponding to the peak is detected.

Figure 5:
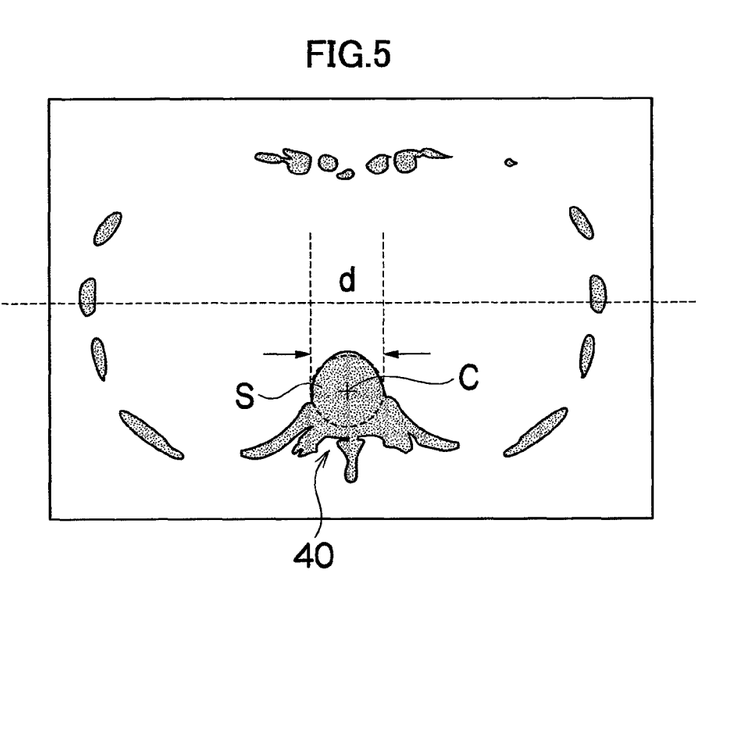
FIG. 5 is an explanatory diagram showing a detection of a vertebral area from the slice image of FIG. 3.

Then, as shown in FIG. 5, a circle S is applied to the upper portion of the detected vertebral area 40 so as to calculate a center C and a width d of the vertebra. The vertebra center C and the vertebra width d are used to recognize a vertebral area, rib areas on the right and left sides, and a sternum area.

Figure 6:
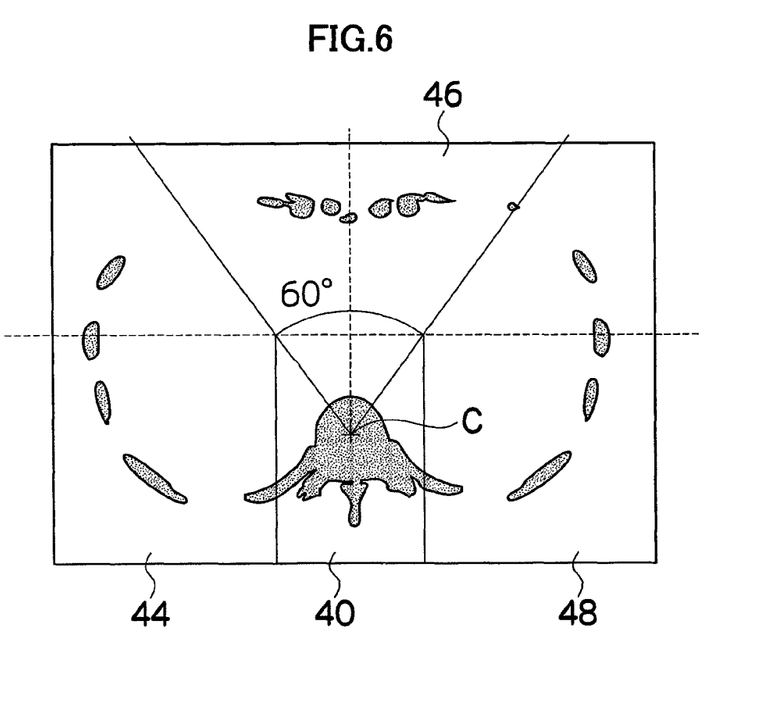
FIG. 6 is an explanatory diagram showing bone sites which are obtained by dividing the bone area in the slice image of FIG. 3.

As shown in FIG. 6, two half lines are drawn upward from the center C of the vertebra obtained by the above calculation to form an angle of 60 degrees therebetween, and also two straight lines are drawn perpendicular to the central line A in the longitudinal direction of the body surface, with the center C of the vertebra being set in the middle therebetween. The distance between the two straight lines is equal to the width of the vertebral area, and is set to be one and a half times that of the above width d.

In this way, the two half lines and the two straight lines perpendicular to the central line A in the longitudinal direction of the body surface are used to divide the CT slice image of FIG. 6 into four areas: a vertebral area 40, a right rib area 44, a sternum area 46, and a left rib area 48.

The bone area in units of pieces recognizing device 22 recognizes a bone in units of pieces such as a vertebra, a right rib, a chest bone, and a left rib. And the bone area in units of pieces recognizing device 22 assigns a different label (number) to each the recognized pieces of bones. The bone area in units of pieces recognizing device 22 also provides a three dimensional table for storing the result of the recognition, and applies the label to each voxel of the corresponding bone area.

The three dimensional data of the result of the bone extraction may be replaced with the result of the recognition.

In the above example, a bone area is recognized in units of pieces such as a vertebra, a right rib, a chest bone, and a left rib, but the recognition unit may be further divided into sub-units, such as a right first rib, a right second rib, a first cervical vertebrae, a second cervical vertebrae, a first thoracic vertebra, and a second thoracic vertebra. That is, similarly, the bone areas of each CT slice image are recognized so as to find a gap between areas having densities of high values, using the characteristics of a bone which is shown to have a density of a rather high value, so that a vertebra can be recognized in detail one by one in units of pieces.

Then, the display site selecting device 23 selects a piece corresponding to the piece to be displayed based on a site which is input by a user via the input device 15. The selection by a user is performed by selecting a predefined site which is comprised of a plurality of pieces.

Figure 7A:
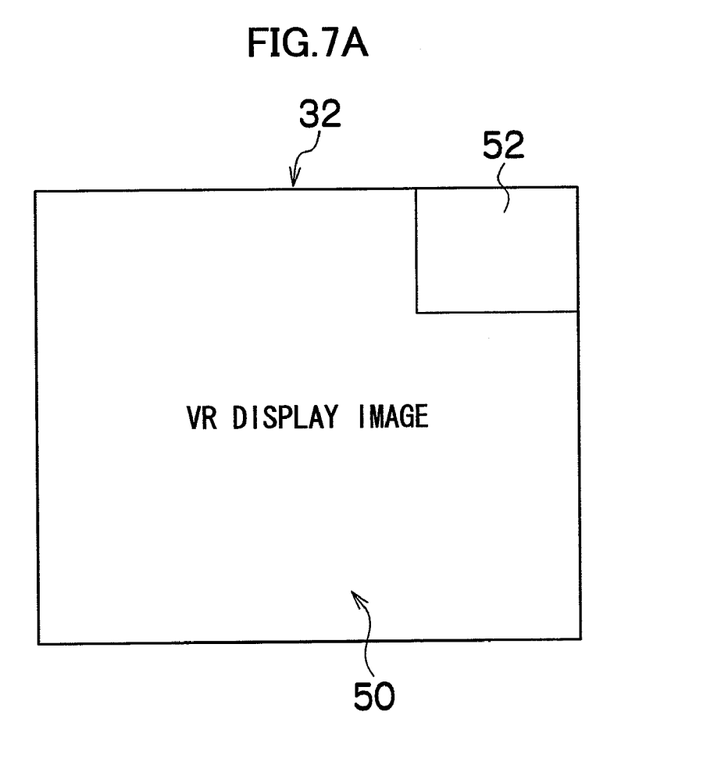
FIG. 7A is an explanatory diagram showing a volume rendering display image.
Figure 7B:
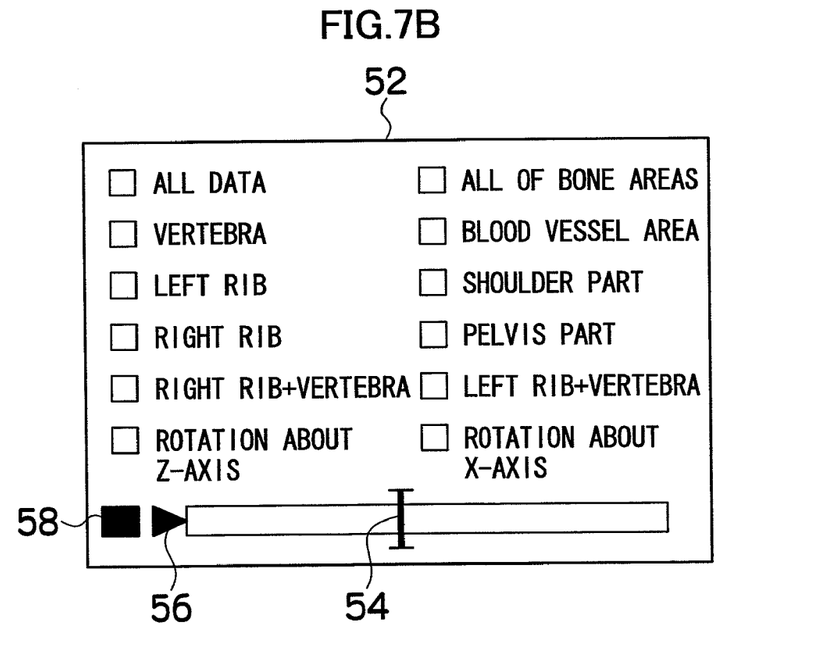
FIG. 7B is an explanatory diagram showing an enlarged site selection display for selecting a bone site to be displayed, on the right side of the rendering display image shown in FIG. 7A.

FIG. 7 shows the way to select a site. As shown in FIG. 7, a volume rendering display image 50 is displayed on the display screen 32 of the image displaying section 30. The volume rendering display image 50 has a display for selection of a site (site selection display) 52 on the upper right corner thereof. The enlarged site selection display 52 is shown on the right side of FIG. 7.

The site selection display 52 displays a list of selectable sites so that a user checks the boxes of the sites he/she wants to display. The user also can specify the rotation direction in which the image is rotated. The rotation direction is for example specified based on the z-axis in the body axis direction of a subject, and the x-axis in the plane of the cross section which is perpendicular to the z-axis.

When a site is specified, only the selected site is displayed on the display screen 32 in units of pieces. The display at the lower part of the site selection display 52 shows a rotation of an image on the screen, and as a user moves an I-shaped cursor 54, the image on the screen is rotated about a specified axis. A click of a triangle mark 56 causes the image on the screen to be automatically rotated, and a click of a square mark 58 causes the rotation to stop. Such rotations about an axis allow the parts which are overlapped to each other or hidden behind other parts to be completely revealed.

The correspondence relationship between site and piece which corresponds to the site is predefined, but a user may define the relationship by newly specifying a piece and specifying a new name of the site which corresponds to the pieces. Moreover, two or more sites may be combined to form a larger site.

Figure 8:
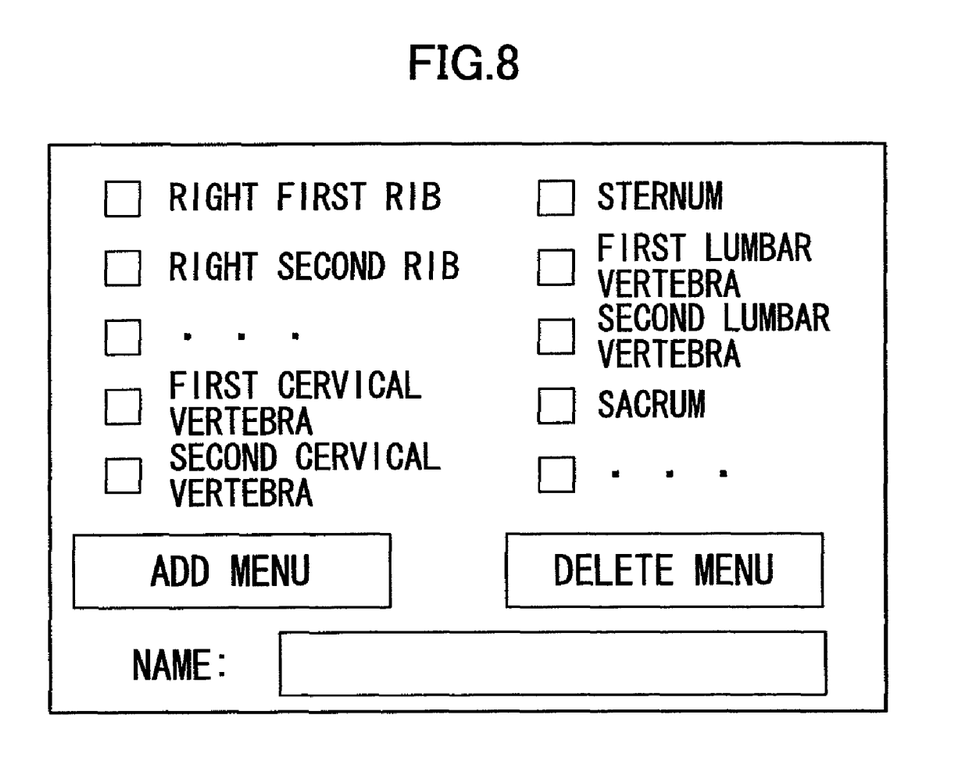
FIG. 8 is an explanatory diagram showing a method for newly defining a correspondence relationship between bone site and bone piece, and editing a piece selection menu by a user.

When a user selects pieces, and specifies a site name for the pieces as described above, in order to edit a piece selection menu, for example in the case of a screen display shown in FIG. 8, the user selects several bone pieces from a list of anatomically classified bone pieces, inputs a site name corresponding to the pieces, and specifies the Add Menu, as the result of that the newly defined site by the user is added to the site selection menu on the site selection display 52 shown in FIG. 7.

To the contrary, in order to delete a site which was specified and registered by a user, the user only clicks a Delete Menu key.

The bone in units of pieces display/non-display determining device 24 is provided with a correspondence relationship table between site and piece, and when a user selects a site, which piece is displayed and which piece is not displayed is determined according to the table. For example, a user specifies a rib, the bone in units of pieces display/non-display determining device 24 determines to display the rib and not to display bones other than the rib.

Figure 9:
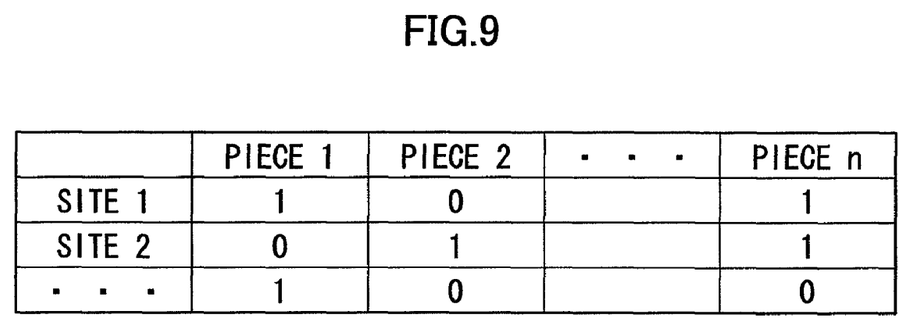
FIG. 9 is an explanatory diagram showing an example of a correspondence relationship table which indicates a correspondence relationship between bone site and bone piece.

FIG. 9 shows an example of a correspondence relationship table which indicates a correspondence relationship between bone sites and bone pieces.

In the table shown in FIG. 9, sites are displayed in the left most column as the items SITE 1, SITE 2, and the like, and pieces are displayed in the upper most row as the items PIECE 1, PIECE 2, and the like, respectively as a list. In the table, with respect to each site, the number 1 is displayed in the box for the corresponding piece, that is, the piece to be displayed, and the number 0 is displayed in the box of the piece not to be displayed.

For example, in FIG. 9, when the site 1 is selected, the piece 1 and the piece n are displayed, and the pieces other than the piece 1 and the piece n are not displayed; while when the site 2 is selected, the piece 2 and the piece n are displayed, and the pieces other than the piece 2 and the piece n are not displayed.

As described above, when a user selects several bone pieces and inputs site names for the pieces, and specifies a menu addition, the correspondence relationship is added to the table for the correspondence relationship between the bone sites and the bone pieces of FIG. 9. In this way, the table for the correspondence relationship between bone sites and bone pieces can be changed via the input device 15 by a user seeing the screen display of FIG. 8.

When the image display in the image displaying section 30 is processed by volume rendering, the display of bone pieces as described above can be achieved by setting the capacity of a voxel corresponding to a displayed piece to be normal, and the capacity of a voxel corresponding to a non-displayed piece to 0 or a lower value than usual.

As described above, in the present embodiment, when a bone area extracted from an X-ray CT image is recognized in units of pieces, and a bone site a user wants to display is selected, a correspondence relationship between site and piece of predefined bones is used so that the bone piece corresponding to the bone site selected by the user is displayed, resulting in that a user only selects a predefine site to readily display a part of the bone he/she wants to display, in units of pieces.

While an image processing apparatus and an image processing method of the present invention have been explained in detail, the present invention is not limited to the above examples, and needless to say, various improvements and modifications may be added without departing from the scope of the present invention.

What is claimed is:

1. An image processing apparatus, comprising:
   a recognizing device which recognizes a bone area extracted from a tomogram, the bone area including a bone site composed of several bone pieces, in units of bone pieces by estimating a range where bone sites of each of vertebra, left and right ribs, and sternum can exist using at least one of an angle formed by straight lines extending from a vertebra center, a vertebra width and a vertebra center on a CT slice image of a vertebra part, and dividing into a plurality of areas composed of vertebra area, left rib area and right rib area, and sternum area using the estimated range;
   a display site selecting device which selects a bone site to be displayed;
   a display/non-display determining device which determines a bone piece to be displayed with respect to the selected bone site; and
   a display controlling device which controls the display site in order to display a bone piece corresponding to the selected bone site based on the determination by the display/non-display determining device, so that a selected bone site is displayed in units of bone pieces merely by selecting the bone site to be displayed.

2. The image processing apparatus according to claim 1, further comprising
   a correspondence relationship table predefining a correspondence relationship between bone site and bone piece to indicate if respective bone piece is to be displayed or not with respect to a bone site, wherein
   the display/non-display determining device determines the bone piece to be displayed with reference to the correspondence relationship table.

3. The image processing apparatus according to claim 2, further comprising
   a changing device which changes the correspondence relationship table.

4. An image processing method, comprising steps of:
   recognizing a bone area extracted from a tomogram, the bone area including a bone site composed of several bone pieces, in units of bone pieces by estimating a range where bone sites of each of vertebra, left and right ribs, and sternum can exist using at least one of an angle formed by straight lines extending from a vertebra center, a vertebra width and a vertebra center on a CT slice image of a vertebra part, and dividing into a plurality of areas composed of vertebra area, left rib area and right rib area, and sternum area using the estimated range;
   selecting a bone site to be displayed on a display site;
   determining a bone piece to be displayed with respect to the selected bone site; and
   controlling the display site in order to display a bone piece corresponding to the selected bone site based on the determination result.

5. A non-transitory recording medium on which a program is recorded, the program causing a computer to realize functions of:
   recognizing a bone area extracted from a tomogram, the bone area including a bone site composed of several bone pieces, in units of bone pieces by estimating a range where bone sites of each of vertebra, left and right ribs, and sternum can exist using at least one of an angle formed by straight lines extending from a vertebra center, a vertebra width and a vertebra center on a CT slice image of a vertebra part, and dividing into a plurality of areas composed of vertebra area, left rib area and right rib area, and sternum area using the estimated range;
   selecting a bone site to be displayed on a display site;
   determining a bone piece to be displayed with respect to the selected bone site; and
   controlling the display site in order to display a bone piece corresponding to the selected bone site based on the determination result.

* * * * *